(12) United States Patent
Schappert

(10) Patent No.: US 6,244,868 B1
(45) Date of Patent: Jun. 12, 2001

(54) INTEGRATED GUIDED-TISSUE-REGENERATION BARRIER FOR ROOT-FORM DENTAL IMPLANTS

(76) Inventor: Douglas Alan Schappert, 802 Temperance Street, Saskatoon, Saskatchewan (CA), S7N 0M8

(*) Notice: Subject to any disclaimer, the term of this patent is extended or adjusted under 35 U.S.C. 154(b) by 0 days.

(21) Appl. No.: 09/581,129
(22) PCT Filed: Dec. 10, 1998
(86) PCT No.: PCT/CA98/01145
  § 371 Date: Jun. 9, 2000
  § 102(e) Date: Jun. 9, 2000
(87) PCT Pub. No.: WO99/29254
  PCT Pub. Date: Jun. 17, 1999

(30) Foreign Application Priority Data

Dec. 10, 1997 (CA) .................................................. 2224332
Apr. 23, 1998 (CA) .................................................. 2235705

(51) Int. Cl.[7] ................................ A61C 8/00; A61C 5/00
(52) U.S. Cl. .............................................. 433/173; 433/215
(58) Field of Search .................................. 433/172, 173, 433/174, 185, 176, 215, 229

(56) References Cited

U.S. PATENT DOCUMENTS 5,759,033 * 6/1998 Elia ....................................... 433/173
5,769,898 * 6/1998 Jisander ................................ 433/173
5,837,278 * 11/1998 Geistlich et al. ..................... 424/444
5,899,697 * 5/1999 Lazzara et al. ....................... 433/173
5,989,026 * 11/1999 Rogers et al. .................... 433/173 X

FOREIGN PATENT DOCUMENTS

2753366 * 9/1996 (FR) .
WO90/07308 * 7/1990 (WO) .
WO97/31586 * 9/1997 (WO) .

* cited by examiner

Primary Examiner—Nicholas D. Lucchesi
(74) Attorney, Agent, or Firm—Michael R. Williams; Adrian D. Battison; Ryan W. Dupuis

(57) ABSTRACT

An integral guided tissue regeneration barrier for root from dental implants is herein described. The barrier is meant to facilitate osseointegration of implants placed with transmucosal healing elements immediately into tooth extraction sites. The barrier comprises an absorbable circumferential membrane arranged to exclude epithelial cells but not osteoblasts from the tooth extraction socket in which the implant is placed. As a result of this arrangement, the implant becomes osseointegrated into the jaw of the patient. If an increase in bone volume around the implant is required, the membrane may be supplemented by a sheet membrane of titanium mesh or foil or absorbable material such as bovine or porcine collagen or synthetic polymer. That is, both the integral guided tissue regeneration barrier and the supplementary sheet membrane are composed of materials that do not need to be removed, thereby reducing to one the number of surgeries required to progress from dentulous site to a site with a loaded implant.

9 Claims, 9 Drawing Sheets

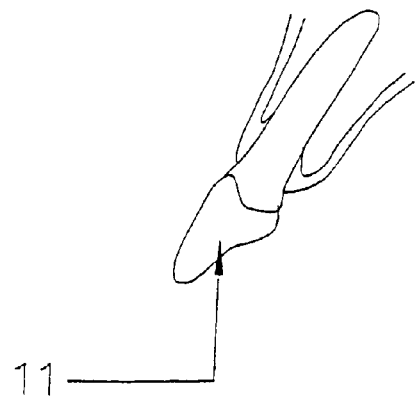
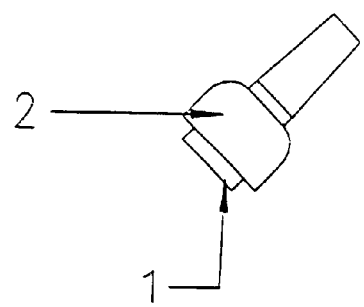
FIG 23
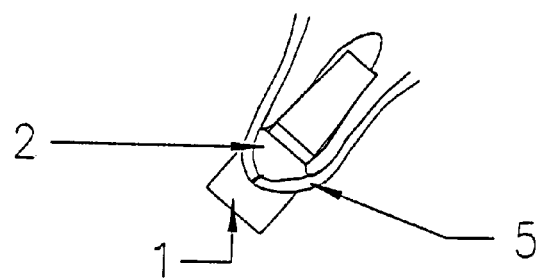
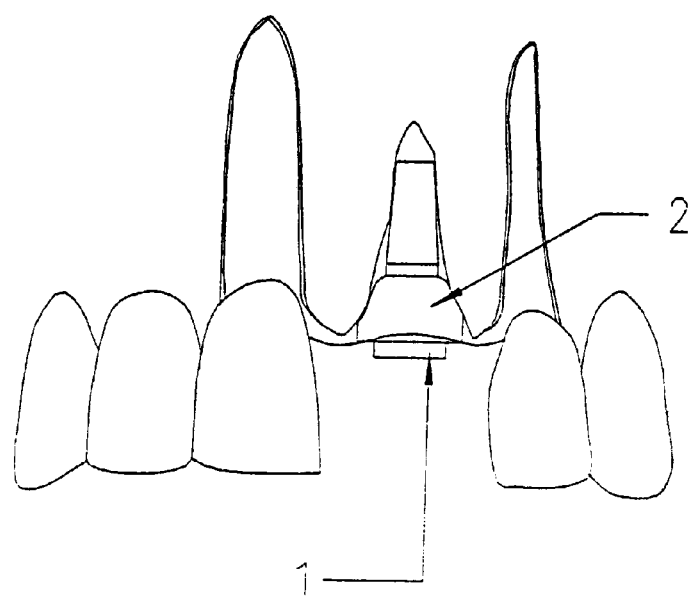

INTEGRATED GUIDED-TISSUE-REGENERATION BARRIER FOR ROOT-FORM DENTAL IMPLANTS

The present invention relates generally to the field of dental implants.

BACKGROUND OF THE INVENTION

Predictably useful dental implants had their beginnings in Sweden in the 1960's in work done by Per-Ingvar Brånemark, who discovered in 1952 that lab animals' bone cells would deposit mineralized bone directly on implanted titanium objects, thereby solidly attaching them to the surrounding bone. He is credited with coining the term osseointegration, which is now in common use, to identify this process. Since his discovery, thousands of titanium implants of mostly screw-type design have been inserted in people's toothless spaces to anchor prosthetic teeth. This implantation has been done almost exclusively by elevating the soft tissue, drilling a hole in bone, placing the implant in the hole, stitching the soft tissue back over the implant, waiting a period of months, re-opening the soft tissue, uncovering the implant and attaching a stud to project through the gum. If bone augmentation has been necessary, yet more operations have been required. If one counts the extraction surgery that leads to most toothless spaces, patients progressing from having teeth, to having a toothless space, to getting an implant and then fastening a prosthetic tooth onto the implant, must submit to at least 3 surgeries. The total rises to 5 if bone augmentation is required and done separately. The number of surgeries would be reduced to one if an implant with a visible trans-mucosal healing element to guide gingival healing, inserted immediately on tooth removal, would osseointegrate. If so, subsequent access to the implant would be non-surgical. Implantation with placement of trans-mucosal elements on extraction would mean that patients would experience fewer painful, expensive and time-consuming surgeries and avoid bone loss in extraction sites, which is associated with problems of appearance, comfort and insufficient bone volume for eventual implants. Furthermore, the patients' periods of wearing temporary prosthetic replacement teeth or doing without teeth altogether would be shorter.

The unpredictability of success with currently available immediate implantation technology has meant that only a small proportion of implants have been placed in tooth sockets immediately after teeth have been removed, and only a small proportion of those have had trans-mucosal elements placed at the time of surgery. The main reason for covering newly-inserted implants with soft tissue during the initial healing phase has been to prevent patients from applying enough force to implants to disrupt bone formation, but prevention of infection has also been a motive, as has been exclusion of mucosal or gingival cells from the implant sites. These potential causes of failure can be controlled without covering the implant initially. Infection prevention is easiest and does not require the present invention. Bacteria can be reduced or eliminated with surgical instruments, sterile technique, antibiotics and antibacterial rinses. Robert Pilliar and others from the University of Toronto have found that implant movements under $50\mu$ can take place without osseointegration being affected. Achieving fixation great enough to keep movements within this range is dependent on gaining intimate adaptation of the implant to the bone of the extraction site and by controlling the size, duration and direction of dislodging forces applied to it. Intimacy of adaptation can be increased by reshaping the extraction site to conform to the implant shape and by forcing the implant tightly into place. A visible trans-mucosal healing abutment attached to the implant at the time of placement would require the patient to avoid biting on it or pushing on it with his tongue to keep implant movements under $50\mu$. However, it is not unlikely that patients who wished to reduce their numbers of surgeries would find it possible to avoid moving visible healing abutments attached to their implants in most situations.

SUMMARY OF THE INVENTION

It is the object of this invention to provide a guided-tissue-regeneration barrier integrated with root-form dental implants to ensure osseointegration by preventing soft tissue deposition and improving implant stability within a tooth extraction socket.

Placing a barrier to prevent migration of selected cell types into selected areas to control tissue formation during healing is termed guided tissue regeneration (GTR). Furthermore, a GTR barrier fixed around an implant would prevent migration of fibroblasts and epithelial cells into the healing socket, preventing fibrous tissue or epithelium from being created there, and allowing slower-migrating bone cells (osteoblasts) to populate the socket and deposit bone throughout, including directly on the surface of the implant, thereby osseointegrating the implant into the jaw to be an anchor for a prosthetic tooth.

The barrier must be deformable and compressible in order to be closely adapted to the crestal portion of the interior of the socket not filled by the implant, and to the crestal bone surrounding the extraction site. It must retain the form into which it is shaped and must likely allow circulation to be established through it in order to allow the mucosal or gingival tissue overlying it to receive its blood supply through the barrier. It must be easy for a surgeon to cut and adapt to the surgical site It must not cause an inflammatory response, so that the overlying mucosa sutured tightly over it will remain firm and capable of stabilizing the barrier, and so that inflammation will not disrupt bone formation around the implant.

By fulfilling these criteria, a barrier securely attached to an implant or healing abutment can also provide a small increase in implant stability.

Ideally, it should be possible to insert implants with predictably successful osseointegration immediately after removal of teeth in tooth sockets with intact bony walls, by performing the two functions of excluding unwanted cells from the extraction socket and increasing the stability of the implant. Extraction sockets with deficient walls, which require increased bone height on portions of their circumferences, may have guided-tissue-regeneration barriers integrated with root-form dental implants supplemented with sheet-form barriers to obtain the desired bone height increase.

The integral guided-tissue-regeneration barrier is made of absorbable material formed circumferentially around the trans-mucosal healing abutment. It can also be formed around the most coronal 1–2 mm of the implant or around both that portion of the implant and an attached trans-mucosal healing abutment. This material will stay in place on the healing abutment and/or implant by virtue of its intimate adaptation (being formed in place with zero clearance) to those pieces. Its malleability and compressibility could be increased by immersion in saline (together with the healing abutment and/or implant) before being placed in the fresh and suitably modified extraction socket, making it pliable. The amount of absorbable material provided will be big enough in width and therefore have sufficient diameter to occupy the space between the implant and the rim of the socket. The barrier will be compressed on insertion of the implant so that its outermost surface will be forced into the shape of the socket rim. The barrier will be great enough in height that some of it will remain coronal to the crest of the alveolar bone once it is inserted. The excess will be able to be trimmed off with a scalpel before the gum is sutured back into place around the healing abutment. The used of absorbable material in this way will have some stabilizing effect on the implant, and be effective in blocking epithelial migration.

Where increased bone volume on one or more aspects of the implant is required, or bony infill is required in the sockets of roots of multi-rooted teeth, this integrated guided-tissue-regeneration barrier for root-form dental implants can be supplemented with a sheet-form barrier made either from a material which would be absorbed after it had served its purpose, or of a material that would remain permanently in place around the implant. There is at present no non-absorbable barrier material that is conventionally being left in place after periodontal or implant-related guided tissue regeneration. Expanded polytetrafluoroethylene, the most common GTR barrier in use over the last 20 years, can be left in place for only a few weeks because of its disadvantages: in common with other textiles, it cannot be formed into a 3-dimensional shape that it will retain, so surgeons cannot place it precisely where they want it; it penetrates the overlying gum in a high proportion of cases because of its tendency to revert to its original flat shape and because blood vessels cannot penetrate it; and it will not support itself over a void and must therefore be supported by another material placed on the bone. It is of note however that polytetrafluoroethylene is useful as a GTR barrier despite its disadvantages because it has pores small enough to prevent cellular migration and because it does not provoke inflammation.

Titanium foil and mesh have been tried as alternatives (Gay et al, 1997, Oral Health, May 1997: p7–18). Both have successfully permitted bone growth, but foil shares expanded polytetrafluoroethylene's propensity to penetrate the overlying gum, and must be removed once the new bone has formed. Mesh, however, has none of the above-mentioned disadvantages. It can be formed into complex three-dimensional shapes, cut to shape, and is rigid enough to support itself over a space in which additional bone volume is desired. It looks to be a useful material for ensuring that osteoblasts can migrate to where they are wanted without having to win a race with faster-moving fibroblasts and epithelial cells. Titanium mesh is being embedded and left permanently in place in people's jaws (and other parts of their bodies) during other types of surgery., Like titanium implants, it does not provoke an inflammatory response in these situations and is well-tolerated by the surrounding tissue. Dr John Gay and his associates in Toronto have used titanium mesh barriers to promote bony infill with GTR. When doing re-entry surgery to remove the barriers, they have noted absence of inflammation, intimate tissue adaptation to the mesh, and a considerable degree of difficulty in removing the mesh. They question whether it is really necessary to remove the titanium mesh barrier material, which they and other surgeons do insert permanently when doing orthognathic surgery, for example.

It could be necessary to stabilize sheet-form membranes with absorbable pins or titanium screws or bone tacks.

According to the invention, there is provided an integral guided-tissue-regeneration barrier for root-form dental implants to be inserted with root-form dental implants and/or their trans-mucosal elements immediately into tooth extraction sockets, said integral guided-tissue-regeneration barrier comprising: an absorbable membrane arranged to be fitted circumferentially around the trans-mucosal healing element and/or implant such that the membrane excludes mucogingival cells but not osteoblasts from migrating into the tooth extraction socket; and an optional supplementary sheet-form membrane arranged to be placed over and around the absorbable membrane and surrounding bone to promote bone height increase where the walls of extraction sockets into which implants are immediately inserted are deficient in height.

The integral guided-tissue-regeneration barrier may be formed directly on the trans-mucosal healing element or the implant coronal to the surface on which osseointegration occurs. The integral guided-issue-regeneration barrier may have sufficient horizontal width to make its diameter great enough to extend to the inner aspect of the extraction socket into which the implant is placed.

The integral guided-tissue-regeneration barrier may be formed of absorbable material, for example, porcine or bovine collagen or synthetic polymers, for example, lactide or glucolide polymers.

The integral guided-tissue-regeneration barrier may include a root-form dental implant or a trans-mucosal healing abutment around which the barrier is formed.

The integral guided-tissue-regeneration barrier may include a detachable handle for positioning the barrier within the tooth extraction socket.

BRIEF DESCRIPTION OF THE DRAWINGS

FIG. 23 is a collection of sketches of an upper incisor tooth and press-fit implants

In the drawings, like characters of reference indicate corresponding parts in the different figures, wherein:

Figure 1:
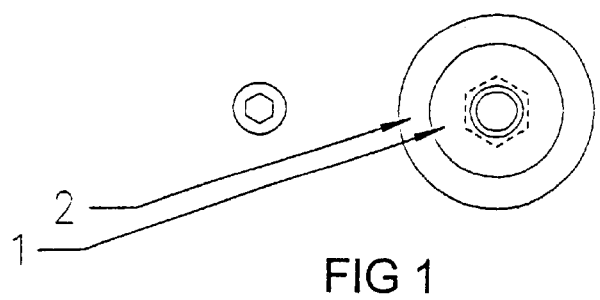
FIG. 1 is a top view of an integral guided-tissue-regeneration barrier attached to a trans-mucosal healing element.
Figure 2:
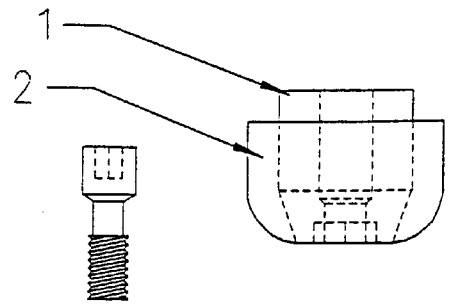
FIG. 2 is a side view of an integral guided-tissue-regeneration barrier attached to a trans-mucosal healing element.
Figure 3:
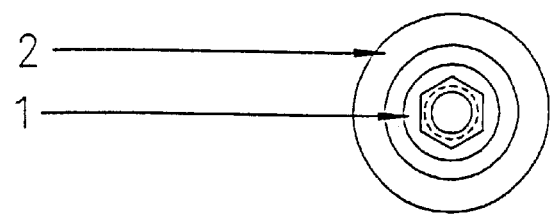
FIG. 3 is a bottom view of an integral guided-tissue-regeneration barrier attached to a trans-mucosal healing element
Figure 4:
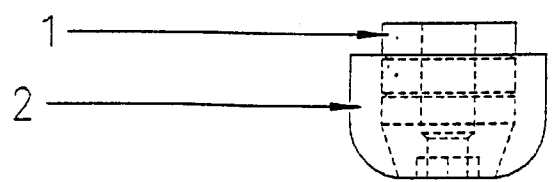
FIG. 4 is a side view of an integral guided-tissue-regeneration attached to a trans-mucosal healing element
Figure 5:
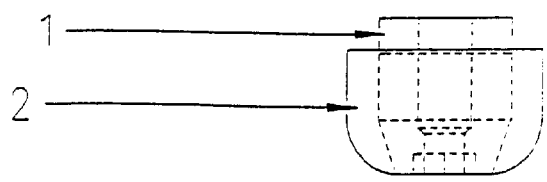
FIG. 5 is a side view of an integral guided-tissue-regeneration attached to a trans-mucosal healing element
Figure 6:
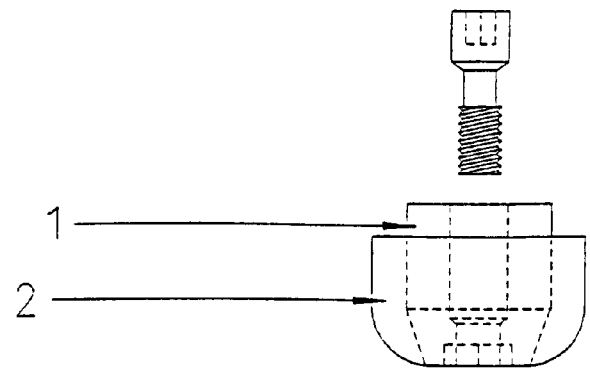
FIG. 6 is a side view of an integral guided-tissue-regeneration attached to a trans-mucosal healing element
Figure 7:
FIG. 7 is a side view of a root-form dental implant of press-fit design
Figure 8:
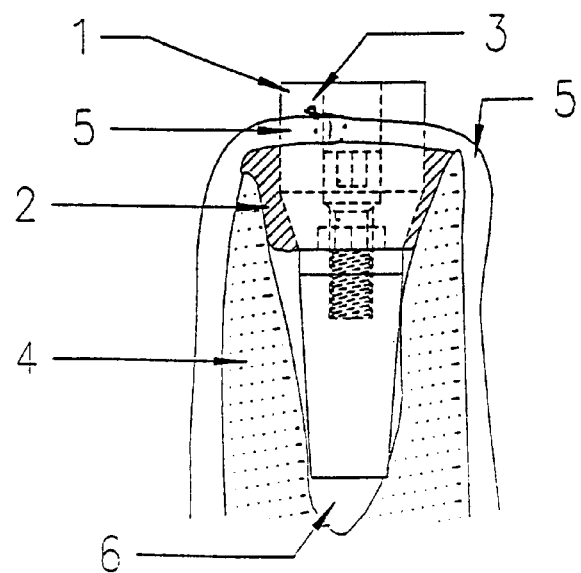
FIG. 8 is a schematic view of a press-fit implant with a trans-mucosal healing element with an integral guided-tissue-regeneration barrier sutured in place in an extraction site with bony walls of adequate height.
Figure 9:
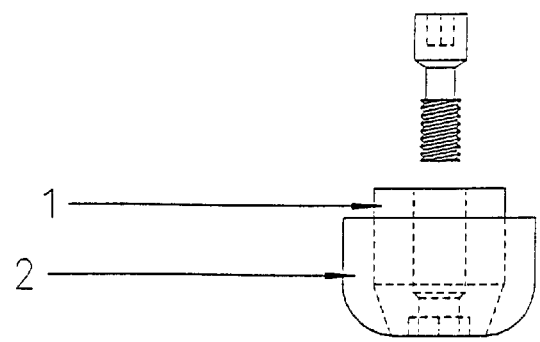
FIG. 9 is a side view of an integral guided-tissue-regeneration attached to a trans-mucosal healing element
Figure 10:
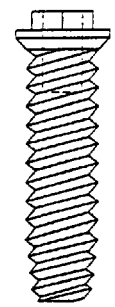
FIG. 10 is a side view of a screw-type dental implant
Figure 11:
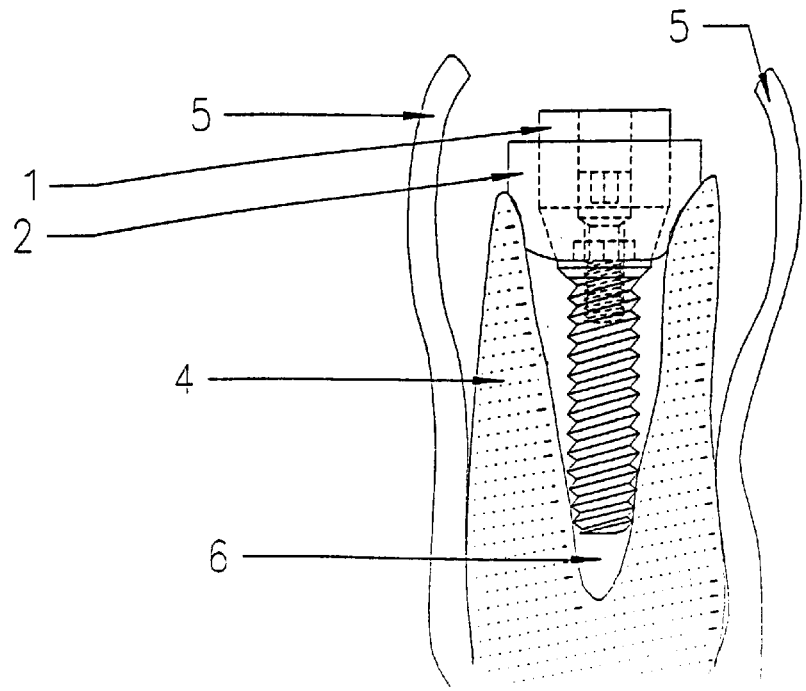
FIG. 11 is a schematic view, before barrier trimming, flap closure and suturing, of a screw-type dental implant with a trans-mucosal healing element with an integral guided-tissue-regeneration barrier in place in an extraction site with bony walls of adequate height.
Figure 12:
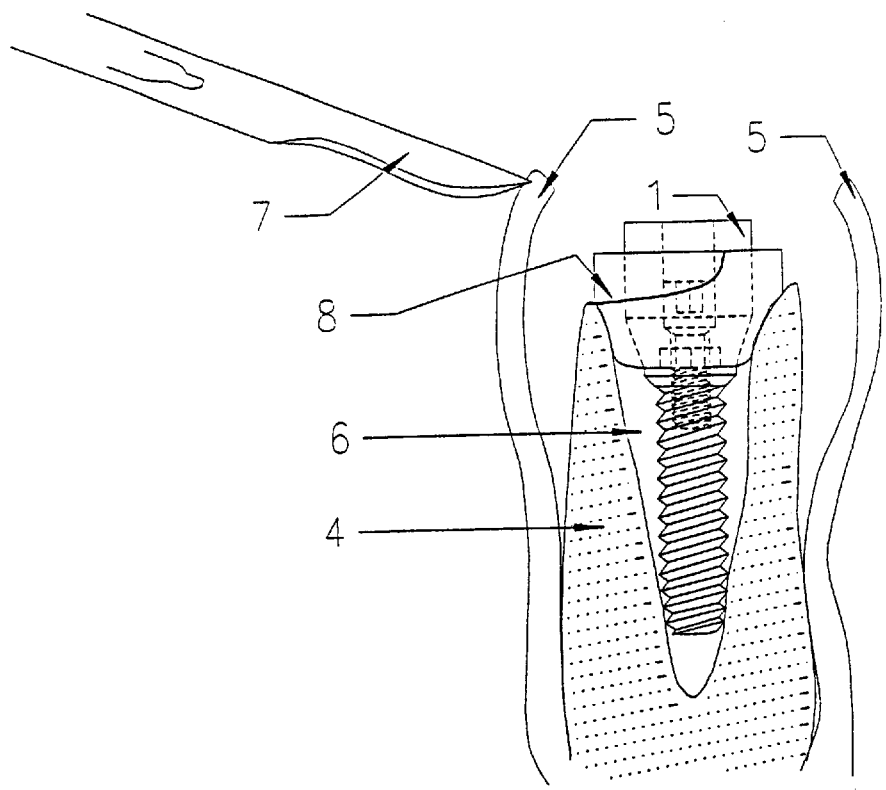
FIG. 12 is a schematic view, after cutting the barrier off at the alveolar crest, but before removal of the barrier piece to be discarded of a screw-type dental implant with a trans-mucosal healing element with an integral guided-tissue-regeneration barrier in place in an extraction site with bony walls of adequate height.
Figure 13:
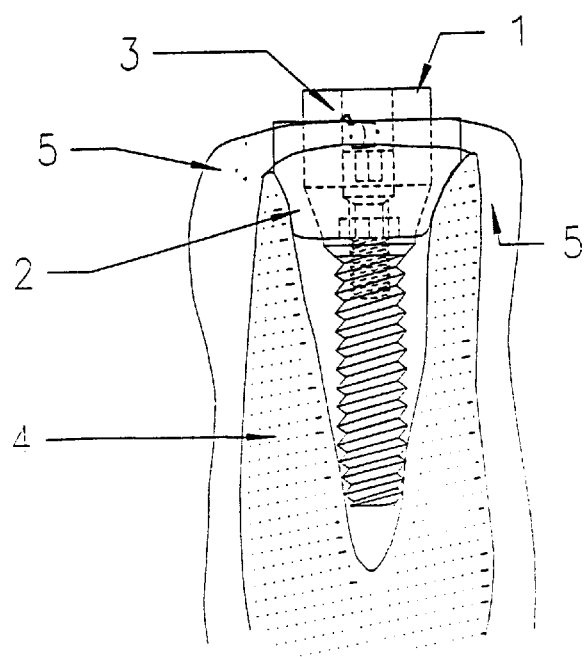
FIG. 13 is a schematic view of a screw-type implant with a trans-mucosal healing element with an integral guidedtissue-regeneration barrier sutured in place in an extraction site with bony walls of adequate height.
Figure 14:
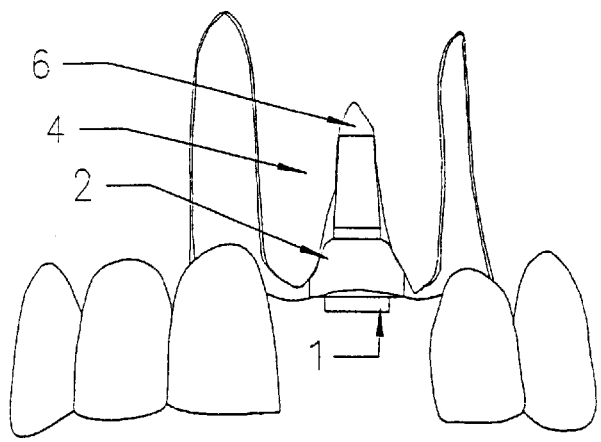
FIG. 14 is a schematic labial view of press-fit implant with a trans-mucosal healing element with an integral guided-tissue-regeneration barrier in place in an extraction site with bony walls of adequate height.
Figure 15:
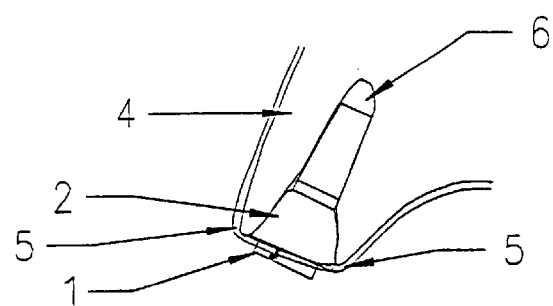
FIG. 15 is a schematic mesial view of a press-fit implant with a trans-mucosal healing element with an integral guided-tissue-regeneration barrier in place in an extraction site with bony walls of adequate height.
Figure 16:
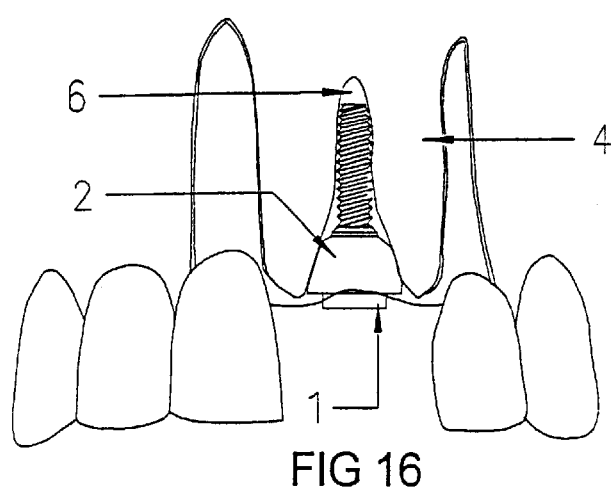
FIG. 16 is a schematic labial view of a screw-type implant with a trans-mucosal healing element with an integral guided-tissue-regeneration barrier in place in an extraction site with bony walls of adequate height.
Figure 17:
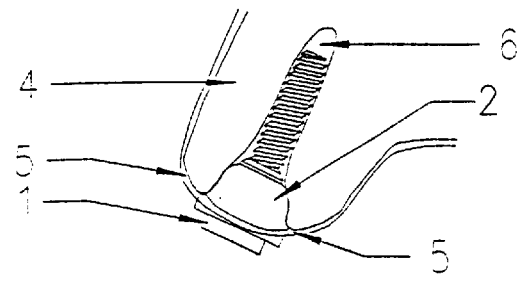
FIG. 17 is a schematic mesial view of a screw-type implant with a trans-mucosal healing element with an integral guided-tissue-regeneration barrier in place in an extraction site with bony walls of adequate height.
Figure 18:
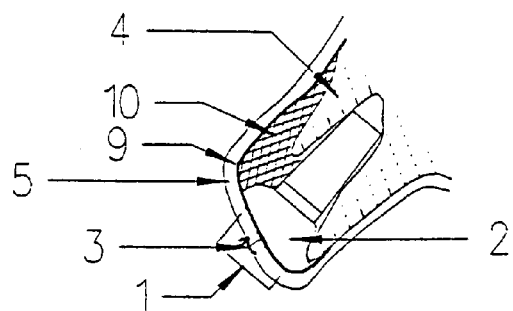
FIG. 18 is a schematic mesial view of a press-fit implant with a trans-mucosal healing element with an integral guided-tissue-regeneration barrier in place in an extraction site with a deficient labial bony wall, and a supplementary sheet-form membrane of titanium mesh in place with bone-graft material beneath it.
Figure 19:
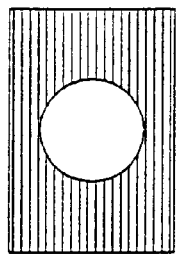
FIG. 19 is a top view of a supplementary sheet-form membrane of titanium mesh.
Figure 20:
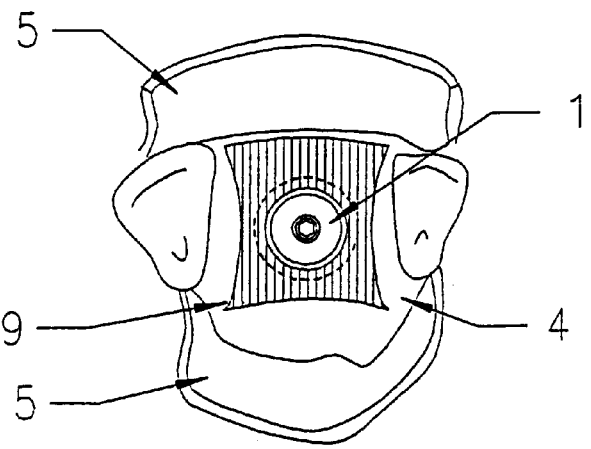
FIG. 20 is a top view of an implant in place in the left upper central incisor position with a titanium mesh supplementary barrier in place around the trans-mucosal healing element, with the mucogingival flap open.
Figure 21:
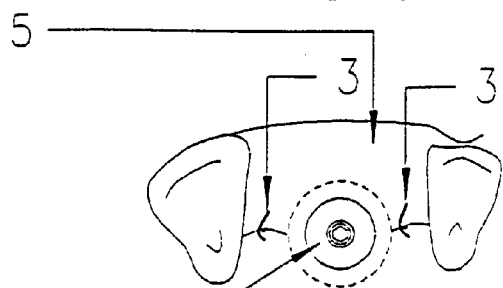
FIG. 21 is a top view of the implant in FIG. 20 with the mucogingival flap sutured into place around the trans-mucosal healing element.
Figure 22:
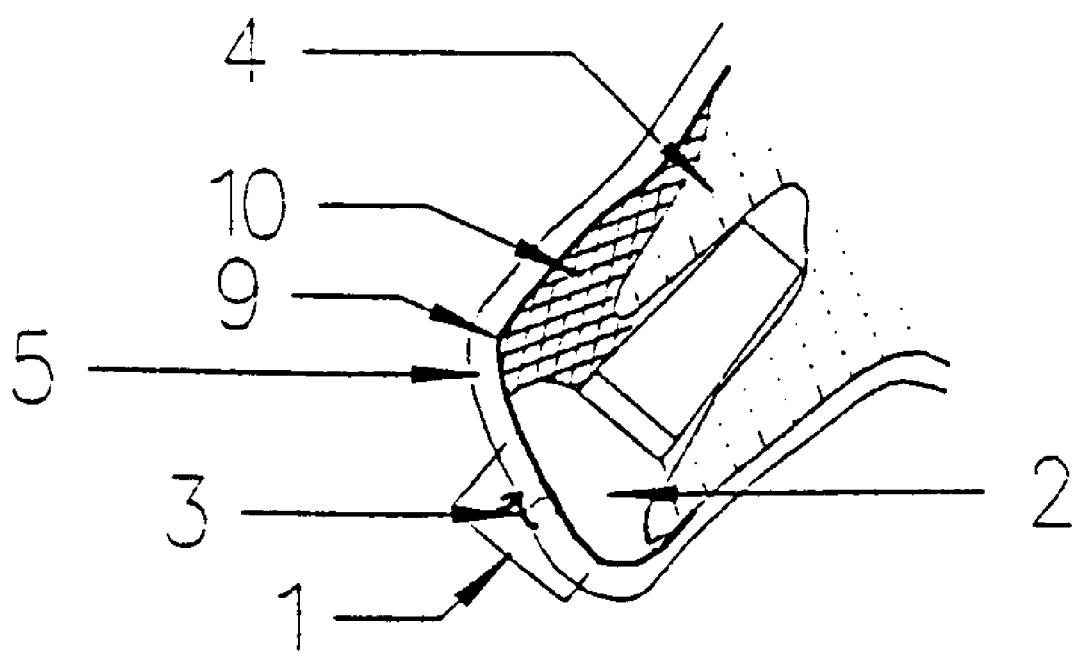
FIG. 22 is a schematic mesial view of a press-fit implant with a trans-mucosal healing element with an integral guided-tissue-regeneration barrier in place in an upper incisor extraction socket with a deficient labial bony wall, with a titanium mesh supplementary barrier in place over labial bone graft material.

| | |
|---|---|
| 1. trans-mucosal healing abutment | 2. absorbable barrier material |
| 3. suture | 4. bone |
| 5. mucogingival flap | 6. extraction socket |
| 7. scalpel blade | 8. crestal cut in absorbable barrier material |
| 9. titanium mesh sheet-form supplementary membrane | |
| 10. bone graft material | 11. incisor tooth |
| 12. disposable plastic handle | 13. sterile disposable blister pack |
| 14. integral guided-tissue-regeneration barrier | |

DESCRIPTION OF THE PREFERRED EMBODIMENTS

A biocompatible material is defined to be one which does not provoke an inflammatory response or a toxic response, is not subject to particulate breakdown, does not provoke an immunogenic response and has a slow enough release of breakdown products for macrophages to phagocytose without producing an inflammatory response.

An absorbable membrane material is defined to be one which can be broken down and removed over time, but which undergoes these processes slowly enough that it serves the function of excluding mucogingival cells from areas where bone formation is wanted until osteoblasts have formed enough mineralized material to give those areas bony character.

The guided-tissue-regeneration membrane may be composed of a plug-shaped mass of absorbable deformable material, for example, bovine tendon collagen formed around the trans-mucosal healing element. It could also be formed around the portion of the implant coronal to the surface on which osseointegration is to take place. The healing element could be screwed into the implant once the implant was placed in the extraction socket. It could also be joined to the implant in lieu of a cover screw and the absorbable guided tissue regeneration barrier material formed around the combination. The absorbable barrier material would be forced into the shape of the socket perimeter as the implant was inserted. The absorbable material would both make a small contribution to the stability of the implant and be an effective barrier to prevent migration of unwanted cell types.

Ideally, the integral guided-tissue-regeneration barrier is left in place to slowly be absorbed after insertion, making reentry surgery to remove it unnecessary. Not only would retrieval of the barrier be unnecessary, but uncovering the implant would be as well. It is intended that the full-thickness flap elevated to expose the bony site for integral barrier placement be sutured around, not over, the implant's trans-mucosal healing element The trans-mucosal healing element would guide the gingival tissue to heal around it so that it would be continuously visible. As a result of this arrangement, it would be painlessly removable and replaceable without local anaesthetic when the time came to attach a prosthesis to the implant.

Titanium mesh could be used to form a supplementary sheet-form integral guided tissue regeneration barrier around the trans-mucosal healing element where bone height of socket walls is inadequate. When used, it would be for the purpose of promoting bone formation to increase the height and bone mass of deficient socket walls.

Integrated barriers in combination with implants would be useful not only in fresh extraction sockets, but also in toothless sites with insufficient bone volume. Using them, bone augmentation, implant insertion and implant exposure could be accomplished with only 2 surgeries, 1 or 2 fewer than current techniques require. The reduction would be possible because the integral barrier would not be removed. The integrated barrier would also make the operations easier and faster for the surgeon.

The range of dental surgeons providing implants with integrated barriers immediately on extraction of teeth could encompass general dentists capable of the limited flap surgery required, as well as periodontists and oral surgeons. This range is wider than the range of simple implant providers, and could potentially increase the number of patients who could benefit from the invention.

If priced correctly, immediate implants with integral GTR barriers would be found preferable to extraction and bridging, complex root canal treatment and toothless spaces. By being low-cost, single-surgery, short-healing-time tooth replacements, they would be apt to make the public more familiar with the benefits and relative ease of implants in general, and would therefore be apt to increase the number of simple implants being placed in edentulous sites.

The function of the integral barrier is to make it possible for the implant portion of the implant-barrier combination to become osseointegrated after having been inserted in a tooth socket immediately after removal of a tooth. It will do this by preventing unwanted cell types from entering and proliferating in the socket and by decreasing the likelihood of movement of the implant in the extraction site.

The integral barrier is to be left in place, in contrast with non-absorbable guided-tissue-regeneration barriers used to increase bone volume for implant insertion.

Root form dental implants with integral guided tissue regeneration barriers, together with supplementary sheet-form barriers, though most useful in fresh extraction sockets, may also be used in edentulous areas to induce bone growth to create increased bone volume where bone height or width were inadequate to envelope the implant.

Preferably, the supplementary barrier is composed titanium mesh or an absorbable membrane made of bovine or porcine collagen or synthetic polymers such as lactide or glucolide polymers, both constructions possessing biocompatibility, the malleability necessary to allow the barrier to be intimately adapted to the bony surface of the alveolar crest and the possibility of being cut to final shape at the time of surgery.

The supplementary sheet-form barrier may be pre-formed in order for it to conform to the shape of the bone of the maxillary or mandibular alveolar crest, thereby reducing the amount of manipulation needed during the surgical procedure in which it is inserted.

The means of joining the absorbable barrier material to the implant or the trans-mucosal healing butment may comprise forming in place, either by itself or together with bonding with an adhesive, or pressing material into grooves on the titanium surface during forming in place. The means of joining the barrier to the implant may comprise in situ screwing of the trans-mucosal healing element with attached absorbable barrier into the implant so that the barrier is in tight apposition to the walls of the extraction socket. Additionally, during the manufacturing process, before sterilization and packaging, rather than at the time of surgery, the absorbable integral guided-tissue-regeneration barrier material could be formed around the already assembled implant-trans-mucosal healing element combination.

The supplementary sheet-form barrier will be pre-sterilized and packaged as a separate element, to remain so until removed from its package at the time of surgery, then cut to final shape and adapted to the bone surrounding the implant site, The sheet-form barrier is put into use by the surgeon cutting and adapting it around the implant in place in the surgical site.

Implant-barrier combinations and trans-mucosal healing element-barrier combinations preferably include removable handles in order for them to be manipulated without actually being touched, so that when the surgeon removes the combination from its sterile packaging at the time of surgery, he can insert the implant in the extraction socket without touching the implant.

Referring to the drawings, an integral guided-tissue-regeneration barrier for root-form dental implants is comprised of membrane material The integral guided-tissue-regeneration barrier 14 is arranged to stabilize the root-form implant member, and to act as a barrier to soft tissue cells, as described below. Specifically, the barrier membrane 2 acts to exclude fibroblasts and epithelial cells from a tooth extraction socket 6.

The implant member of the implant-barrier combination is arranged to be inserted into a tooth extraction socket 6 as described below. The details of the implant member are not shown as these are known to persons knowledgeable in the art.

Figure 24:
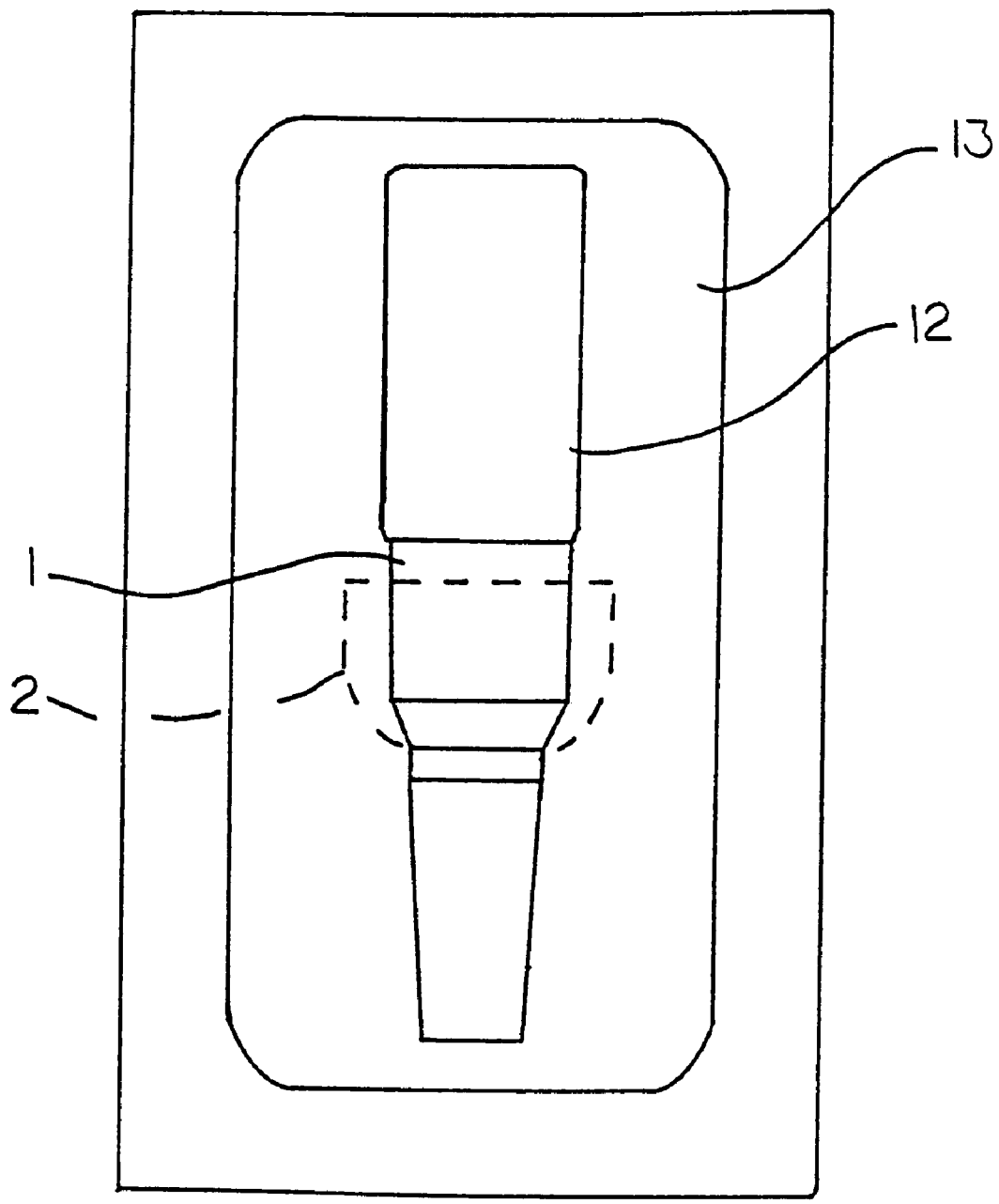
FIG. 24 is a schematic view of a press-fit implant with a trans-mucosal healing element with an integral guided-tissue-regeneration barrier attached to a disposable plastic handle in a disposable sterile blister pack.

The integral guided-tissue-regeneration barrier 14 may be attached to a root-form dental implant prior to packaging or at the time of surgery. Assembly is by connecting the implant member to the barrier 14 such that the barrier 14 extends outwardly from the implant member. When the implant member is inserted in the barrier 14 at the time of surgery, the implant member is held in the barrier 14, for example, by the closeness of the fit of a barrier collar to the implant. Alternatively, in some embodiments, the implant member is bonded to the barrier 14 with an epoxy adhesive. Alternatively, the implant member may be connected to the barrier 14 by other means, for example, by welding the barrier 14 to the implant member. It is of note that, once assembled, the dental implant-barrier combination may be sterilized and enclosed in sterile packaging 13 for later use, as shown in FIG. 24. This in turn will greatly reduce the risk of bacterial contamination and surface contamination of the barrier 14 and implant member.

In another embodiment shown in FIG. 24, the dental implant-barrier combination may include a removable handle 12 for aiding in manipulating the dental implant-barrier combination during surgery.

In operation the surgeon evaluates the site clinically before tooth extraction and views the radiograph image to determine whether the tooth is replaceable with an implant-barrier combination and if so, what size implant the combination should have. The surgeon will also determine the likelihood of having to add a supplementary sheet-form GTR barrier to promote bone formation to replace deficient socket walls so that the implant's osseointegration surface is completely surrounded by bone. At the time of surgery, the surgeon elevates a mucogingival flap 5 about the tooth, removes the tooth, mechanically debrides the socket 6, confirms (or modifies) the implant choice and shapes the extraction socket to receive the implant, taking care to insert the implant deeply enough to allow for the creation of attractive contours of any prosthesis to be attached to the implant after osseointegration. If the trans-mucosal healing element was combined with the implant in the sterile packaging, the surgeon will have inserted it together with the implant. If not, the surgeon will evaluate the site to determine the length of healing element required and screw the healing element, with its integral guided-tissue-regeneration barrier to place on the implant in situ. Before inserting the barrier, either attached to the implant or a separate healing element, the surgeon will hydrate the barrier in saline prior to insertion to increase its pliability. On insertion of the barrier, the surgeon will ensure that it contacts the interior of the socket all around its circumference. Specifically, the amount of absorbable material provided must be big enough in diameter to occupy the space between the implant and the rim of the socket, and compressible so that on insertion of the implant, the outermost surface of the barrier would be forced into the shape of the socket rim. The surgeon will have taken care to avoid handling either the implant surface or the barrier, holding the combination by the attached handle 13 so as not to touch or contaminate those surfaces. The surgeon then completes the shaping of the integral guided-tissue-regeneration barrier 2 by cutting away that portion of it crestal to the surface of the bony walls of the socket. The surgeon will evaluate the need for a supplementary sheet-form GTR barrier. If one is required due to insufficient enclosure of the implant by the bony walls of the socket, he will choose a sheet-form barrier, cut it to shape, form it into the correct shape and fix it in place about the healing element over the absorbable integral barrier. It may be necessary to attached the supplementary membrane to bone with tiny titanium screws or tacks or absorbable pins. The surgeon will then suture the mucogingival flap in place around the implant healing element.

Both the absorbable integral barrier membrane and the supplementary sheet-form membrane are biocompatible and create little risk of infection, as noted above. The absorbable integral membrane and the sheet-form supplementary membrane will retain their formed shapes and circulation can be established through them. Consequently, unlike expanded polytetrafluoroethylene and titanium foil, the muco-gingival flap will heal into place around the healing element and over the barriers. As a result of their biocompatibiliy, small risk of infection, shape retention and possibility of establishment of circulation, the integral guided-fissue-regeneration barrier 2 and supplementary sheet-form barrier do not have to be removed in a subsequent surgical procedure. As a result of the barrier 2 preventing migration of fibroblasts and epithelial cells into the extraction socket 6, osteoblasts populate the healing blood clot around the implant member 14, achieving osseointegration. Once osseointegration has occurred, the healing element can be removed non-surgically, without anaesthetic, and a prosthetic abutment and a prosthesis can be attached to the implant.

Since various modifications can be made in my invention as herein described, and many apparently widely different embodiments of the same made within the spirit and scope of the claims without departure from such spirit and scope, it is intended that all matter contained in the accompanying specification shall be interpreted as illustrative only and not in a limiting sense.

What is claimed is:

1. A combination transmucosal healing element/absorbable guided tissue regeneration barrier for placement into a tooth extraction socket along with a root-form dental implant, on removal of a tooth, comprising:
   a transmucosal healing element, and
   an absorbable guided tissue regeneration barrier, fitted around the trans-mucosal healing element,
   wherein the guided tissue regeneration barrier is a plug-shaped mass that is inserted into the tooth extraction socket.

2. The combination of claim 1 wherein the absorbable guided tissue regeneration barrier is composed of a biocompatible, absorbable material such as porcine or bovine collagen, or a synthetic polymer of lactide, glucolide or a combination thereof.

3. The combination of claim 1, wherein the guided tissue regeneration barrier component has sufficient horizontal width to extend to the inner aspect of the extraction socket into which the combination is placed along with the implant.

4. The combination of claim 1, wherein the guided tissue regeneration barrier deformable and compressible.

5. The combination of claim 1 wherein the absorbable guided tissue regeneration barrier is formed directly on the transmucosal healing element.

6. The combination of claim 1 wherein the transmucosal healing element includes connectors for attaching the combination to the implant.

7. The combination of claim 1 including an implant connected to the transmucosal healing element for simultaneous insertion into an extraction socket.

8. The combination of claim 1 including a disposable handle attached to the transmucosal healing element for manipulating the combination during insertion of the combination into the extraction socket.

9. The combination of claim 1 wherein the combination is packaged in a sterile container for keeping the combination sterile prior to use.

* * * * *